United States Patent
Morton et al.

(10) Patent No.: US 12,354,587 B2
(45) Date of Patent: *Jul. 8, 2025

(54) BROAD SPECTRUM INSTABILITY DETECTION AND MITIGATION

(71) Applicant: BOSE CORPORATION, Framingham, MA (US)

(72) Inventors: Douglas George Morton, Southborough, MA (US); Emery M. Ku, Sudbury, MA (US)

(73) Assignee: Bose Corporation, Framingham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/744,448

(22) Filed: Jun. 14, 2024

(65) Prior Publication Data

US 2024/0339102 A1 Oct. 10, 2024

Related U.S. Application Data

(63) Continuation of application No. 17/460,865, filed on Aug. 30, 2021, now Pat. No. 12,051,398.

(51) Int. Cl.
*G10K 11/178* (2006.01)

(52) U.S. Cl.
CPC .. *G10K 11/17835* (2018.01); *G10K 11/17825* (2018.01); *G10K 11/17881* (2018.01); *G10K 2210/1081* (2013.01); *G10K 2210/3023* (2013.01); *G10K 2210/3026* (2013.01); *G10K 2210/3027* (2013.01); *G10K 2210/3044* (2013.01)

(58) Field of Classification Search
CPC ....... G10K 11/17835; G10K 11/17825; G10K 2210/503
See application file for complete search history.

(56) References Cited

U.S. PATENT DOCUMENTS

| 4,538,296 | A | 8/1985 | Short et al. |
| 5,809,152 | A | 9/1998 | Nakamura et al. |
| 10,244,306 | B1 | 3/2019 | Ku et al. |
| 10,714,072 | B1 | 7/2020 | Bodon et al. |
| 12,051,398 | B2 * | 7/2024 | Morton ............... H04R 1/1041 |
| 2012/0140943 | A1 | 6/2012 | Hendrix et al. |
| 2014/0294191 | A1 | 10/2014 | Parkins |

(Continued)

FOREIGN PATENT DOCUMENTS

| GB | 2234881 A | 2/1991 |
| JP | H10171467 A | 6/1998 |
| JP | H10187201 A | 7/1998 |

(Continued)

OTHER PUBLICATIONS

International Search Report and Written Opinion for International Application No. PCT/US2022/039238 Mailed Nov. 25, 2022, 9 pages.

*Primary Examiner* — Ping Lee
(74) *Attorney, Agent, or Firm* — Patterson + Sheridan, LLP

(57) ABSTRACT

A method performed by an audio output device is provided for detecting instabilities and taking mitigating actions. Specifically, an A-weighted dBA level of a raw feedback signal exceeding a threshold level trigger, at least, muting the driver. The described methods apply to detecting instabilities across a broad frequency spectrum.

20 Claims, 2 Drawing Sheets

(56) References Cited

U.S. PATENT DOCUMENTS

2018/0225082 A1  8/2018  An et al.
2020/0366986 A1  11/2020  Ono

FOREIGN PATENT DOCUMENTS

| JP | 2012226366 A | 11/2012 |
| JP | 2016029510 A | 3/2016 |
| JP | 2020501178 A | 1/2020 |
| WO | 2019039128 A1 | 2/2019 |

* cited by examiner

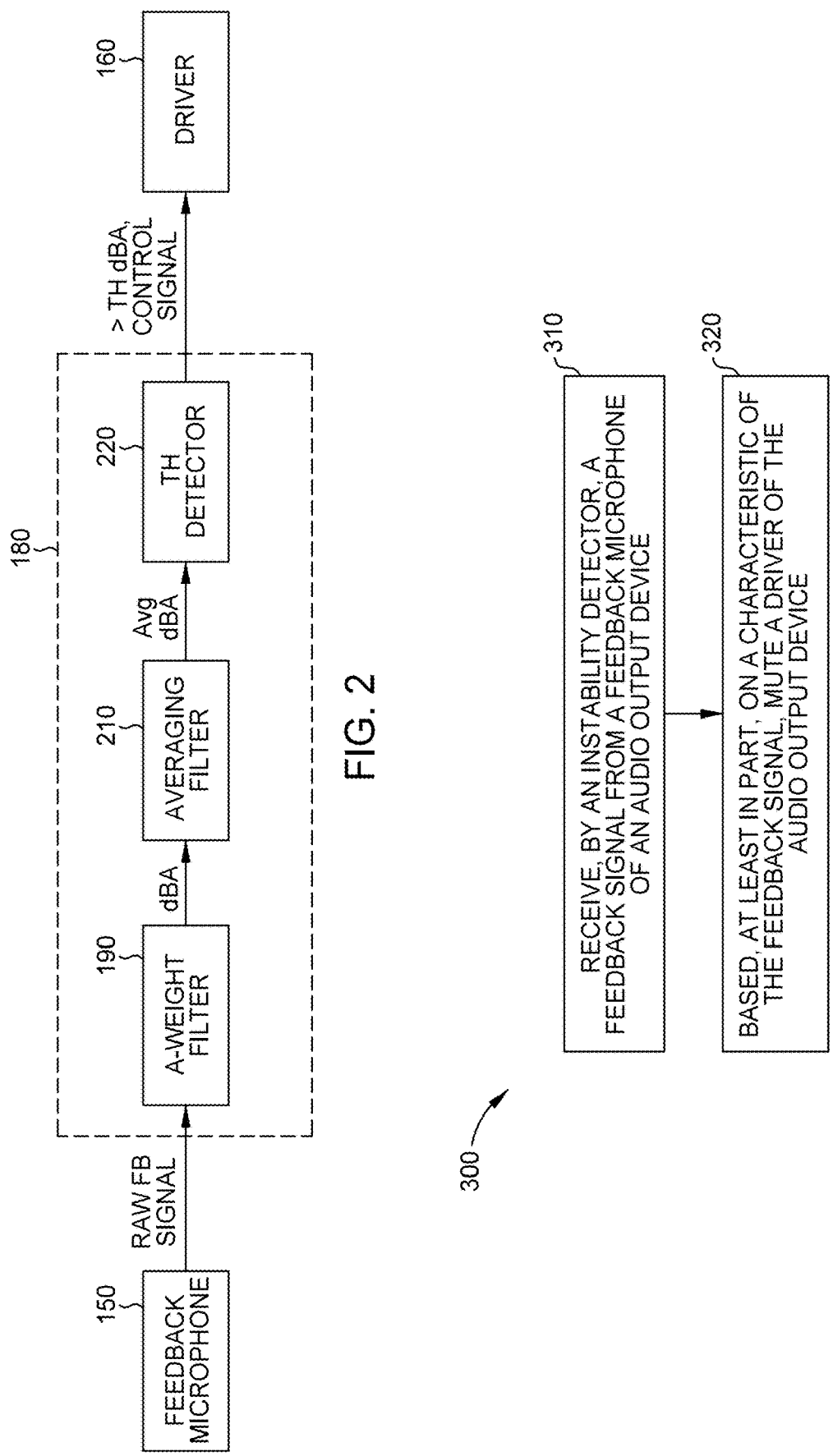

BROAD SPECTRUM INSTABILITY DETECTION AND MITIGATION

CROSS-REFERENCE TO RELATED APPLICATION

This application is a continuation of U.S. patent application Ser. No. 17/460,865, filed Aug. 30, 2021, which is incorporated by reference herein in its entirety.

FIELD

Aspects of the disclosure generally relate to detecting instability in a wearable audio output device and taking action to mitigate the instability. The detection occurs across the human audible frequency spectrum. Mitigating the instability reduces the likelihood of unstable conditions in the device generating a loud noise that is uncomfortable to a user.

BACKGROUND

Various audio devices incorporate active noise reduction (ANR) features, also known as active noise control or cancellation (ANC), in which one or more microphones detect sound, such as exterior acoustics captured by a feedforward microphone or interior acoustics captured by a feedback microphone. Signals from a feedforward microphone and/or a feedback microphone are processed to provide anti-noise signals to be fed to an acoustic transducer (e.g., a speaker, a driver) to counteract noise that may otherwise be heard by a user. Under certain unstable conditions may occur which may be uncomfortable to the user. Thus, it is desirable to detect instabilities and take action to mitigate the instabilities.

SUMMARY

All examples and features mentioned herein can be combined in any technically possible manner.

Aspects provide a method performed by an audio output device comprising: receiving, by an instability detector, a feedback signal from a feedback microphone of the audio output device, and based, at least in part, on a characteristic of the feedback signal, muting a driver of the audio output device.

In aspects, the characteristic of the feedback signal comprises the feedback signal exceeding a threshold A-weighted decibel (dBA) level. In aspects, the feedback signal exceeds the threshold A-weighted decibel (dBA) level for a pre-determined period of time.

In aspects, the feedback microphone detects signals between 20 Hz to 24 kHz.

In aspects, muting the driver comprises muting the driver for a predetermined amount of time.

In aspects, the method further comprises triggering a restart of the audio output device based, at least in part, on the characteristic of the feedback signal. In aspects, the method further comprises triggering the restart when the driver has been muted based, at least in part, on the characteristic of the feedback signal, a threshold number of times over a defined period of time.

In aspects, the method further comprises turning off at least one of the feedback microphone or a feedforward microphone based, at least in part, on the characteristic of the feedback signal.

Aspects provide an audio output device comprising a memory coupled to at least one processor in a first ear piece, the memory having instructions stored thereon for causing the audio output device to: receive, by the at least one processor, a first feedback signal from a first feedback microphone, and based, at least in part, on a characteristic of the first feedback signal, mute a first driver of the audio output device.

In aspects, the characteristic of the first feedback signal comprises the first feedback signal exceeding a threshold A-weighted decibel (dBA) level. In aspects, the feedback signal exceeds the threshold A-weighted decibel (dBA) level for a pre-determined period of time.

In aspects, the first feedback microphone detects signals between 20 Hz to 24 kHz.

In aspects, the instructions to mute comprise instructions for muting the driver for a predetermined amount of time.

In aspects, the instructions further cause the audio output device to trigger a restart of the audio output device based, at least in part, on the characteristic of the first feedback signal. In aspects, the instructions further comprise instructions to cause the audio output device to trigger the restart when the first driver has been muted based, at least in part, on the characteristic of the first feedback signal, a threshold number of times over a defined period of time.

In aspects, the instructions further comprise instructions to cause the audio output device to turn off at least one of the first feedback microphone based or a first feedforward microphone in the first ear piece, at least in part, on the characteristic of the first feedback signal.

In aspects, the audio output device further comprises at least one processor in a second ear piece, the memory having instructions stored thereon for causing the audio output device to receive, by the processor in the second ear piece, a second feedback signal from a second feedback microphone, and based, at least in part, on a characteristic of the second feedback signal, mute a second driver of the audio output device.

In aspects, the instructions cause the audio output device to mute the first driver and the second driver independently.

Aspects provide an audio output device, comprising a feedback microphone, a driver, and an instability detector, the instability detector configured to receive a feedback signal from the feedback microphone of the audio output device and based, at least in part, on a characteristic of the feedback signal, triggering a muting of the driver.

In aspects, the characteristic of the feedback signal comprises the feedback signal exceeding a threshold A-weighted decibel (dBA) level for a predetermined amount of time.

The details of one or more implementations are set forth in the accompanying drawings and the description below. Other features, objects, and advantages will be apparent from the description and drawings, and from the claims.

BRIEF DESCRIPTION OF THE DRAWINGS

FIG. 2 illustrates example components of an instability detector, in accordance with aspects of the disclosure.

FIG. 3 illustrates example operations performed to detect and mitigate an instability, in accordance with aspects of the disclosure.

DETAILED DESCRIPTION

Figure 1:
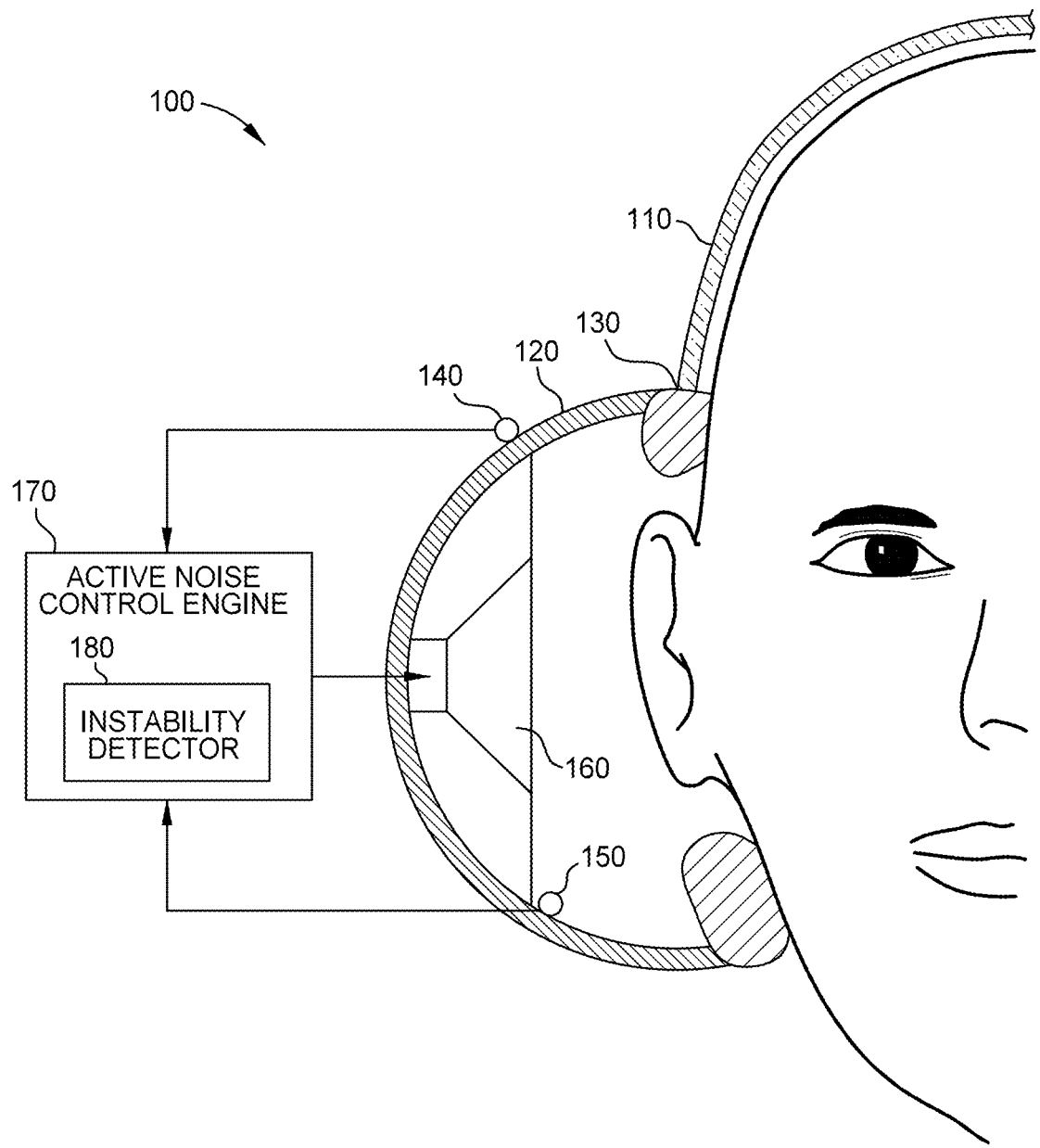
FIG. 1 illustrates an example audio output device in which aspects of the disclosure may be practiced.

Aspects of the present disclosure provide an audio output device and methods performed by an audio output device to detect and mitigate instabilities in the device. Currently, a specific sub-set of instabilities that result in oscillations may be detected. In one example, at least a portion of a feedback signal is processed to detect a tonal signature of an unstable condition within a portion of the signal captured by a feedback (e.g., internal) microphone. If the tonal signature represents an unstable condition, the audio output device generates one or more control signals to adjust an ANC system such that the unstable condition is mitigated.

Current methods may be limiting because they attempt to detect and are responsive to a sub-set of known or otherwise pre-identified instabilities. Further, it is desirable to reduce or stop the instability as quickly as possible so as to reduce the possibility of discomfort and hearing damage. The audio output devices, and methods described herein, detect instabilities across a broad frequency spectrum in a lightweight manner. The instabilities may be detected before the oscillation gets to the point of damaging the listener's hearing.

Any change in the transfer function between either a feedback microphone and a driver or between the a feedforward microphone and the driver can create an instability. Example causes of instabilities across the spectrum of audible frequencies include the nozzle of an in-ear tip being blocked, removing an ear-cup covering of a feedback microphone, 150, cupping the opening of the ear-cup by a user's hand, and crushing or damaging the housing and electronics in the device.

FIG. 1 illustrates an example of an ANC system 100 deployed in a headphone 110. The headphone 110 includes an ear-cup 120 on each side, which fits on, around or over the ear of a user. The ear-cup 120 may include a layer 130 of soft material (e.g., soft foam) for a comfortable fit over the ear of the user. The ANC system on the headphone 110 includes a feedforward microphone (or external microphone) 140 disposed on or near the outside of the ear-cup 120 to detect ambient noise in the user's environment. The ANC system also includes a feedback microphone (or internal microphone) 150 which may be positioned proximate (e.g., within a few millimeters) to the user's ear canal and/or a driver 160. The driver 160 can be an acoustic transducer for conversion of an electrical signal, into an acoustic signal that the user may hear. In aspects, the driver 160 radiates audio signals from an audio source device that the headphone 110 is connected to. The feedforward microphone 140, the feedback microphone 150, and the driver 160 are connected to an active noise control engine 170.

The ANC system 100 operates to reduce acoustic noise components heard by a user of the audio output device. Noise cancelling systems may include feedforward and/or feedback systems. In a feedforward system, the feedforward microphone 140 detects noise external to the headphone 110. The active noise control engine 170 provides an anti-noise signal to counter the external noise expected to be transferred through to the user's ear. In a feedback system, the feedback microphone 150 detects acoustic signals reaching the user's ear. The active noise control engine 170 processes the detected signals to counteract any signal components not intended to be part of the user's acoustic experience.

In aspects, the active noise control engine 170 includes an instability detector 180. The instability detector 180 detects a feedback signal from the feedback microphone 150. Based on a characteristic of the feedback signal, the instability detector 180 takes action to mitigate an instability. In aspects, the instability detector 180 identifies an instability in the feedback signal output by the feedback microphone 150 and takes action to, at least, mute the driver 160.

FIG. 1 illustrates some example components of a headphone 110. Other components, not illustrated in FIG. 1, may be present for the headphones 110 to function. The headphones 110 may further include hardware and circuitry including processor(s)/processing system and memory configured to implement one or more sound management capabilities or other capabilities including, but not limited to, ANC and the methods described for detecting and mitigating instabilities.

For example, the headphones 110 include (or are coupled to) a processor and memory storing instructions for operating the headphones and the methods described herein.

Further, FIG. 1 illustrates a right side portion of the headphones. A corresponding, non-illustrated, left side portion of the headphones 110 includes similar features as illustrated in FIG. 1. Notably, the left side may also include a feedforward microphone, feedback microphone, driver, active noise control engine, and instability detector. Similar to the right portion of the headphones, a left side instability detector detects a feedback signal from the feedback microphone positioned proximate (e.g., within a few millimeters) to the user's loft car canal and/or a driver in the left ear-cup. Based on a characteristic of the feedback signal, the instability detector takes action to mitigate an instability, such as muting the driver in the left ear-cup.

In aspects, the right side and the left side of the headphones 110 each independently determines if an instability is detected in a respective ear-cup. The instability detector in the right ear-cup controls the driver on the same side (e.g., right side) of the headphone 110. Similarly, the instability detector in the left ear-cup controls the driver on the same side (e.g., left side) of the headphones 110. Thus, a raw feedback signal from a respective feedback microphone is independently processed to identify an instability for the respective side of the headphones 110. Based on the respective feedback signal, one or more of the drivers are independently controlled and/or muted.

While FIG. 1 illustrates an example where the ANC system 100 is deployed in an around-ear headphone 110, the ANC system 100 could also be deployed in other form-factors, including in-ear headphones, on-ear headphones, and audio eyeglasses or frames.

FIG. 2 illustrates example components of the instability detector 180, according to aspects of the present disclosure. The instability detector 180 receives a raw feedback signal from the feedback microphone 150. The instability detector 180 performs an A-weighting (A-frequency weighting) to weight the audible frequencies to reflect the response or sensitivity of the human ear to noise. An A-weighting filter 190 encompasses the full audible frequency range from 20 Hz to 24 kHz and the output approximates the frequency sensitivity of the human ear. A-weighting accounts for the relative loudness perceived by the human ear, as the ear is less sensitive to low audio frequencies. An n-second averaging filter 210 averages the A-weighted signal over a predetermined period of time. A threshold detector 220 compares the averaged A-weighted signal to a threshold dBA level. As described below, when the threshold detector 220 determines the averaged A-weighted signal exceeds a threshold dBA level, a control signal is output to, at least, mute the driver 160.

The instability detector 180 detects an instability when the averaged A-weighted signal from the feedback microphone exceeds a threshold A-weighted level (dBA) for the predetermined period of time. In response to detecting the instability, the instability detector 180 transmits a control signal to mute the driver 160 for a period of time. After the period of time elapses, the driver unmutes. The instability detector does not take any action to effect the driver unless an instability is detected. Temporarily muting the driver protects the user by cutting off sound from the driver and allowing the user to distance the headphones from the user's ear.

The International Telecommunications Union standard ITU-T H.870 "Guidelines for safe listening devices/systems" describes requirements for safe-listening devices and systems, including personal/portable audio systems, to protect people from hearing loss. The objective of the standard is to provide a means to determine when a listener has experienced a maximum dosage over a given period of time. ITU-T H.870 specifies the time to reach the dosage amount of 1.6 $Pa^2h$ per week for adults for a given A-weighted level (dBA) as shown in the table below. Generally, the time halves for every 3 dBA. For 110 dBA, the time to reach the dosage amount of 1.6 $Pa^2h$ per week for an adult is approximately 2.25 min and for 120 dBA, the time is a few seconds. Given the short amount of time needed to reach the maximum dosage, it is important that people are not unnecessarily exposed to high dBA levels and that any such exposure is limited as much as possible.

| dB(A) SPL | Weekly (1.6 $Pa^2h$) |
|---|---|
| 107 | 4.5 min |
| 104 | 9.5 min |
| 101 | 19 min |
| 98 | 37.5 min |
| 95 | 75 min |
| 92 | 2.5 h |
| 89 | 5 h |
| 86 | 10 h |
| 83 | 20 h |
| 80 | 40 h |

In aspects, the threshold A-weighted level is 110 dBA. In aspects, the averaging filter 210 is a 1 second averaging filter. Therefore, in one example, the A-weighted signal must exceed 110 dBA for 1 second for the instability detector to detect an instability.

In an example, upon detecting the instability, the instability detector mutes the driver for 3 seconds. After muting for 3 seconds, the driver unmutes.

An A-weighted level of 110 dBA averaged over 1 second triggering a mitigation action for 3 seconds is based on many factors. As shown in the table above, ITU-T H.870 specifies the listening time for an average adult is 40 hours/week at 80 dBA and that the time drastically decreases for higher SPLs (e.g., listening time is only 4.5 minutes/week at 107 dBA). An average adult should be exposed to no more than 2.25 minutes/week at 110 dBA. Using a 1 second averaged dBA level trigger to detect an instability is significantly quicker than outlined by the standard while still preventing very short term transient noises from triggering an instability. Additionally, the 1 second averaging takes into account processing time for the instability detector to perform A-weighting and confirm the threshold dBA level has been met. Therefore, the A-weighted level of 110 dBA for 1 second is a balance of an excessively loud signal for a short amount of time to minimize the discomfort and hearing damage and avoid short term transient noises from triggering an instability.

Muting the driver for 3 seconds allows the user to take the headphones off of the user's head or move the headphones away from the user's ear, and take actions to stop the instability. Muting for 3 second further allows the user to place the device back on and resume listening or turn off the headphones if the user is not able to stop the instability. While muting is one action that may be taken based on a detected instability, other actions may be performed as described in more detail with respect to FIG. 3.

FIG. 3 illustrates example operations 300 performed by an audio output device to detect and mitigate instabilities. At 310, an instability detector of an audio output device receives a feedback signal from a feedback microphone of the audio output device. Based on a characteristic of the feedback signal, at 320, the driver is muted. In aspects, the instability detector transmits a control signal to mute the driver.

The feedback microphone detects signal between 20 Hz and 24 kHz such that the instability detection occurs across the human audible frequency spectrum, which is generally capped at 20 KHz. Additionally, the instability detection is not limited to a specific subset of known instabilities. In aspects, the characteristic of the feedback signal comprises an A-weighted dBA level exceeding a threshold level. In one example, the feedback signal exceeds the threshold dBA level for a pre-determined period of time.

Examples describe using a 110 dBA level threshold; however, instability detection may use other threshold levels greater than or less than 110 dBA. Similarly, examples describe the average A-weighted feedback signal exceeding the threshold for a 1 second; however, other periods of time, greater than or less than 1 second, may be used in accordance with the methods described herein. Generally, a high average dBA level for a short amount of time identifies an instability quickly enough to minimize discomfort and avoid hearing loss.

In aspects, the driver is muted for a predetermined amount of time. According to the examples described above, the driver is muted for 3 seconds. The user may assume that the audio device has stopped outputting sounds due to an instability, as opposed to a loss of connection to a source device, in part because of the momentarily loud sound the user heard prior to the driver muting. In aspects, the instability detector transmits a control signal to mute the driver for a configured amount of time. The driver may be muted for any amount of time (more than or less than 3 seconds), so long as the time the driver is muted allows the user to take off the audio output device or otherwise distance the audio output device from the user's ear.

In aspects, the instability detector tracks the number of instabilities or the number of times the instability detector transmits an indication to mute the driver. In aspects, the audio output device forces a restart of the device after a configured number of instabilities are detected over a period of time. For example, if n instabilities are detected over a period of time (e.g., 1 day), or the instability detector transmits y control signals to mute the driver in response to instabilities in a period of time (e.g., 4 hours), the audio output device may trigger the device to restart, in an effort to refresh the system and/or install updates to help address any issues that may be causing the frequent instabilities.

In aspects, the feedback microphone and/or the feedforward microphone is turned off after a configured number of instabilities over a period of time are detected. Turning off the feedback microphone breaks the signal path between of the feedback microphone and driver, thereby preventing further excessively loud signals to be output by the driver. Turning off the feedforward microphone will stop oscillations and instabilities that may be caused by a feedforward signal. The muting, forced restart, turning off the feedback microphone, and turning off the feedback microphone may be performed alone or in in any combination.

The detection and mitigation methods described herein are advantageously not limited to a subset of instabilities. Instead, the methods detect instabilities across a broad frequency spectrum. In aspects, an instability triggers muting the driver. Additionally or alternatively to muting the driver, an instability (or a number of instabilities over a given amount of time) may force the device to restart. Additionally or alternatively to muting and/or restarting the device, the feedback microphone and/or feedforward microphone may be turned off such that a feedback or feedforward signal is not transmitted to the driver and output to the user.

It can be noted that, descriptions of aspects of the present disclosure are presented above for purposes of illustration, but aspects of the present disclosure are not intended to be limited to any of the disclosed aspects. Many modifications and variations will be apparent to those of ordinary skill in the art without departing from the scope and spirit of the described aspects.

In the preceding, reference is made to aspects of the disclosure. However, the scope of the present disclosure is not limited to specific described aspects. Aspects of the present disclosure can take the form of an entirely hardware embodiment, an entirely software embodiment (including firmware, resident software, micro-code, etc.) or an embodiment combining software and hardware aspects that can all generally be referred to herein as a "component," "circuit," "module" "system" or "unit". Furthermore, aspects of the present disclosure can take the form of a computer program product such as a computer program tangibly embodied in an information carrier, such as one or more non-transitory computer-readable media or storage device having readable program code embodied thereon.

Any combination of one or more computer readable medium(s) can be utilized. The computer readable medium can be a computer readable signal medium or a computer readable storage medium. A computer readable storage medium can be, for example, but not limited to, an electronic, magnetic, optical, electromagnetic, infrared, or semiconductor system, apparatus, or device, or any suitable combination of the foregoing. More specific examples of a computer readable storage medium include: an electrical connection having one or more wires, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination the foregoing. In the current context, a computer readable storage medium can be any tangible media that can store a program.

The flowchart and block diagrams in the Figures illustrate the architecture, functionality and operation of possible implementations of systems, methods and computer program products according to various aspects. In this regard, each block in the flowchart or block diagrams can represent a module, segment or portion of code, which comprises one or more executable instructions for implementing the specified logical function(s). In some alternative implementations the functions noted in the block can occur out of the order noted in the figures. For example, two blocks shown in succession can, in fact, be executed substantially concurrently, or the blocks can sometimes be executed in the reverse order, depending upon the functionality involved. Each block of the block diagrams and/or flowchart illustrations, and combinations of blocks in the block diagrams and/or flowchart illustrations can be implemented by special-purpose hardware-based systems that perform the specified functions or acts, or combinations of special purpose hardware and computer instructions.

What is claimed is:

1. An audio output device, comprising:
   an internal microphone, a driver, and an instability detector, the instability detector configured to:
   receive a feedback signal from the internal microphone of the audio output device;
   trigger muting of the driver based, at least in part, on a first number of instabilities detected over a first configured period of time; and
   after muting the driver, trigger a restart of the audio output device based on at least a second number of instabilities detected from the internal microphone over a second configured period of time or the triggering of the mute of the driver, wherein the second configured period of time is different than the first configured period of time, and the second number of instabilities is different than the first number of instabilities.

2. The audio output device of claim 1, wherein the instability detector is further configured to trigger muting of the driver based, at least in part, on a characteristic of the feedback signal, wherein the characteristic of the feedback signal comprises the feedback signal exceeding a threshold A-weighted decibel (dBA) level, and wherein the threshold A-weighted dBA level is between 90 dBA and 130 dBA.

3. The audio output device of claim 2, wherein the characteristic of the feedback signal comprises the feedback signal exceeding the threshold A-weighted dBA level for a pre-determined period of time.

4. The audio output device of claim 3, wherein the pre-determined period of time is between 0.1 seconds and 10 seconds.

5. The audio output device of claim 1, wherein the internal microphone is configured to detect signals between 20 Hz and 24 kHz.

6. The audio output device of claim 1, wherein the instability detector is configured to mute the driver for a time between 1 and 10 seconds.

7. The audio output device of claim 1, wherein the first number of instabilities is associated with a threshold number of detected instabilities over a defined period of time.

8. The audio output device of claim 1, wherein the internal microphone comprises a feedback microphone.

9. The audio output device of claim 8, wherein the instability detector is further configured to:
   turn off at least one of the feedback microphone or a feedforward microphone based, at least in part, on the first number of instabilities detected over the first configured period of time.

10. The audio output device of claim 1, wherein an instability of the first number of instabilities occurs due to a change in a transfer function between the internal microphone and a driver of the audio output device or between a feedforward microphone and the driver of the audio output device.

11. The audio output device of claim 1, wherein an instability of the first number of instabilities occurs due to a blockage of a nozzle of an in-ear tip of the audio output device.

12. The audio output device of claim 1, wherein the instability detector is further configured to:
   restart the internal microphone or a feedforward microphone based on at least a third number of instabilities detected over a third configured period of time, wherein the third configured period of time is different than both the first configured period of time and the second configured period of time.

13. A method performed by an audio output device, the method comprising:
receiving, with an instability detector, a feedback signal from an internal microphone of the audio output device;
triggering a muting of a driver of the audio output device based, at least in part, on a first number of instabilities detected over a first configured period of time; and
after the muting of the driver, triggering a restart of the audio output device based on at least a second number of instabilities detected over a second configured period of time or the triggering of the muting of the driver, wherein the second configured period of time is different than the first configured period of time, and the second number of instabilities is different than the first number of instabilities.

14. The method claim 13, wherein triggering the muting of the driver is further based, at least in part, on a characteristic of the feedback signal, wherein the characteristic of the feedback signal comprises the feedback signal exceeding a threshold A-weighted decibel (dBA) level, and wherein the threshold A-weighted dBA level is between 90 dBA and 130 dBA.

15. The method of claim 14, wherein the characteristic of the feedback signal comprises the feedback signal exceeding the threshold A-weighted dBA level for a pre-determined period of time, and wherein the pre-determined period of time is between 0.1 seconds and 10 seconds.

16. The method of claim 13, wherein muting the driver comprises muting the driver for a time between 1 and 10 seconds.

17. A non-transitory computer-readable medium comprising computer-executable instructions that, when executed by one or more processors of an audio output device, individually or collectively, cause the audio output device to perform a method, the method comprising:
receiving, by the one or more processors, a feedback signal from a first internal microphone;
triggering a muting of a driver of the audio output device based, at least in part, on a first number of instabilities detected over a first configured period of time; and
after muting the driver, trigger a restart of the audio output device based on at least a second number of instabilities detected from the first internal microphone over a second configured period of time or the triggering of the mute of the driver, wherein the second configured period of time is different than the first configured period of time, and the second number of instabilities is different than the first number of instabilities.

18. The non-transitory computer-readable medium of claim 17, wherein triggering the muting of the driver is further based, at least in part, on a characteristic of the feedback signal, wherein the characteristic of the feedback signal comprises the feedback signal exceeding a threshold A-weighted decibel (dBA) level, and wherein the threshold A-weighted dBA level is between 90 dBA and 130 dBA.

19. The non-transitory computer-readable medium of claim 18, wherein the characteristic of the feedback signal comprises the feedback signal exceeding the threshold A-weighted decibel (dBA) level for a pre-determined period of time, and wherein the pre-determined period of time is between 0.1 seconds and 10 seconds.

20. The non-transitory computer-readable medium of claim 17, wherein muting the driver comprises muting the driver for a time between 1 and 10 seconds.

* * * * *